(12) United States Patent
Feldman et al.

(10) Patent No.: US 9,636,060 B2
(45) Date of Patent: May 2, 2017

(54) DERMAL LAYER ANALYTE SENSING DEVICES AND METHODS

(71) Applicant: ABBOTT DIABETES CARE INC., Alameda, CA (US)

(72) Inventors: Benjamin Jay Feldman, Berkeley, CA (US); Hyun Cho, Berkeley, CA (US); John Charles Mazza, Long Beach, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 442 days.

(21) Appl. No.: 14/108,964

(22) Filed: Dec. 17, 2013

(65) Prior Publication Data

US 2014/0171771 A1    Jun. 19, 2014

Related U.S. Application Data

(60) Provisional application No. 61/738,776, filed on Dec. 18, 2012.

(51) Int. Cl.
*A61B 5/05* (2006.01)
*A61B 5/1473* (2006.01)
*A61B 5/145* (2006.01)

(52) U.S. Cl.
CPC .......... *A61B 5/1473* (2013.01); *A61B 5/1451* (2013.01); *A61B 5/14532* (2013.01)

(58) Field of Classification Search
USPC ................................. 600/309, 345, 347, 365
See application file for complete search history.

(56) References Cited

U.S. PATENT DOCUMENTS

| 4,627,445 A | * | 12/1986 | Garcia | A61B 5/1411 600/583 |
|---|---|---|---|---|
| 5,807,375 A | * | 9/1998 | Gross | A61K 9/0021 600/309 |
| 6,706,049 B2 | | 3/2004 | Moerman | |
| 7,509,153 B2 | | 3/2009 | Blank et al. | |
| 2004/0096959 A1 | | 5/2004 | Stiene et al. | |
| 2005/0054908 A1 | | 3/2005 | Blank et al. | |
| 2010/0312314 A1 | | 12/2010 | Ice et al. | |
| 2010/0326842 A1 | * | 12/2010 | Mazza | A61B 5/14532 205/777.5 |
| 2010/0331642 A1 | * | 12/2010 | Bruce | A61B 5/6846 600/345 |
| 2011/0319738 A1 | * | 12/2011 | Woodruff | A61B 5/14532 600/365 |

(Continued)

FOREIGN PATENT DOCUMENTS

| WO | WO 89/11820 A1 | 12/1989 |
|---|---|---|
| WO | WO 03/080169 A1 | 10/2003 |
| WO | WO 2006/122048 A1 | 11/2006 |

OTHER PUBLICATIONS

WO, PCT/US2013/075658 IPRP, Jun. 23, 2015.

(Continued)

*Primary Examiner* — Michael Kahelin
*Assistant Examiner* — Mitchell E Alter
(74) *Attorney, Agent, or Firm* — One LLP

(57) ABSTRACT

Provided are dermal sensors and dermal sensor applicator sets to insert at least a portion of a dermal sensor into a dermal layer of a subject, as well as methods of making and using the same.

29 Claims, 9 Drawing Sheets

(56) References Cited

U.S. PATENT DOCUMENTS

2012/0078071 A1 3/2012 Bohm et al.

OTHER PUBLICATIONS

WO, PCT/US13/75658 ISR, Mar. 11, 2014.
Ali, S., "Finite Element Modeling of Dermally-Implanted Enzymatic Microparticle Glucose Sensors", Thesis Submitted to the Office of Graduate Studies of Texas A&M University bearing a date of Aug. 2010.
EP, 13865733.3 Supplementary Search Report, Jul. 13, 2016.

* cited by examiner

A

B

C

DERMAL LAYER ANALYTE SENSING DEVICES AND METHODS

CROSS-REFERENCE TO RELATED APPLICATIONS

This application claims the benefit of and priority to U.S. Provisional Application No. 61/738,776, filed Dec. 18, 2012 and titled "Dermal Layer Analyte Sensing Devices and Methods," which is incorporated by reference herein in its entirety for all purposes.

FIELD

The subject matter described herein relates to devices and methods for the performance of in vivo analyte sensing in a subject.

BACKGROUND

The detection of the level of glucose or other analytes, such as lactate, oxygen or the like, in certain individuals is vitally important to their health. For example, the monitoring of glucose is particularly important to individuals with diabetes. Diabetics may need to monitor glucose levels to determine when insulin is needed to reduce glucose levels in their bodies or when additional glucose is needed to raise the level of glucose in their bodies.

Devices have been developed for the in vivo continuous monitoring of analytes such as glucose in bodily fluid such as in the blood stream or in interstitial fluid over a period of time. These analyte measuring devices include in vivo analyte sensors that are positioned in vivo, i.e., below a skin surface of a user in a blood vessel or in the subcutaneous tissue of a user during the testing.

Blood vessel sensors are more invasive than subcutaneous sensors, but have the advantage of providing analyte concentrations directly from the blood. Subcutaneous analyte sensors are therefore used, but they too have certain limitations. For example, the insertion of the analyte sensor in the subcutaneous tissue results in skin/tissue trauma that causes immunological response that can cause inaccurate sensor readings, at least for a period of time. For example in the case of glucose sensors, the trauma may cause an over-consumption of glucose in the positioned sensor vicinity by erythrocytes released by localized bleeding. Further, the glucose response from a subcutaneously positioned sensor lags the response of a venous-positioned sensor, primarily due to a physiological lag between subcutaneous and venous glucose.

It would therefore be desirable to have devices and methods that address these issues and that could accurately monitor analyte levels, such as glucose, in areas of the body other than blood vessels or the subcutaneous tissue. Analyte sensors, applicators for inserting them, and methods of making and using are described that provide benefits of blood vessel and subcutaneous analyte sensors without their key limitations.

SUMMARY

Provided herein are embodiments of in vivo analyte sensors and in vivo sensor applicator sets that insert at least a sensing portion of an in vivo analyte sensor into a subject. Also provided are embodiments of methods of using the sensor applicator sets to insert a sensing portion of an in vivo analyte sensor into a subject, and methods of determining in vivo analyte presence and concentration using the in vivo analyte sensors. Although these embodiments will be described mainly with respect to a dermal sensor inserted into a dermal layer of a subject, it should be noted that the sensors can be used in other tissue as well. Many of these dermal embodiments have the conveniences and advantages of being operable when positioned in the dermal layer rather than in a blood vessel, but retain or improve upon the accuracy of a blood vessel sensor. For example, many of these embodiments do not exhibit the extent of physiological lag that is experienced by sensors positioned in the subcutaneous space.

DETAILED DESCRIPTION

Figure 1:
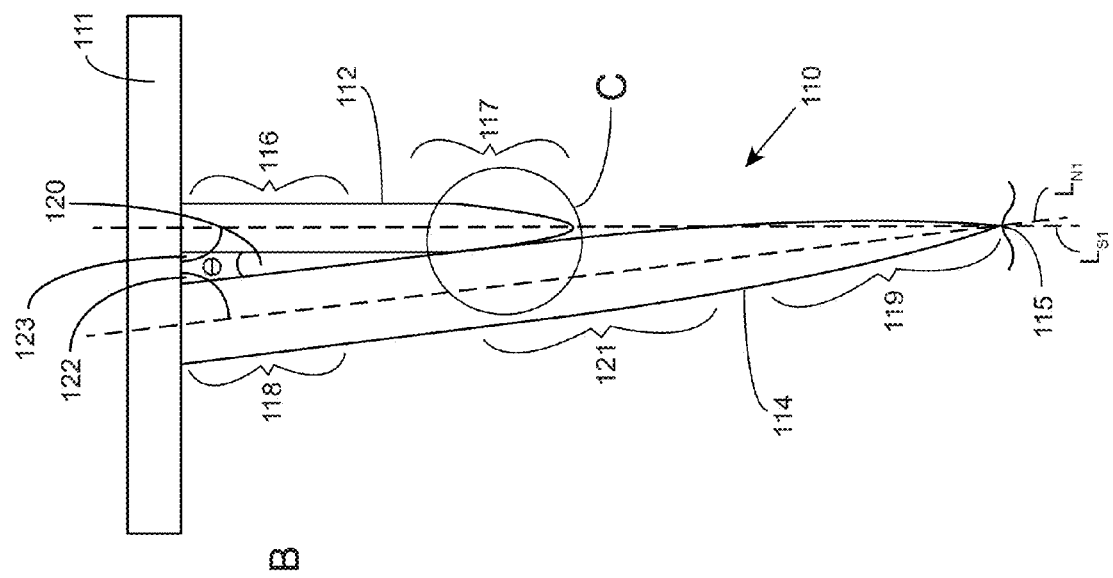
FIG. 1 schematically illustrates alternative sensor applicator set configurations. In Panel A, the longest axis of the insertion needle is disposed substantially parallel to the longest axis of the sensor. In Panel B, which schematically illustrates a sensor applicator set according to one embodiment of the present disclosure, the longest axis of the insertion needle is disposed at an angle relative to the longest axis of the sensor.
Figure 1:
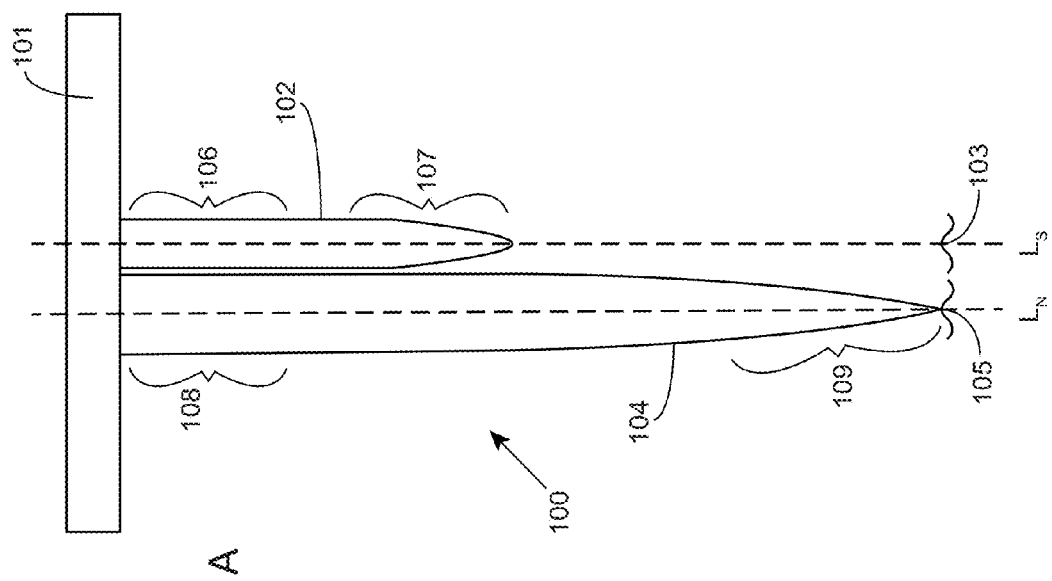

Before the sensor applicator sets and methods of the present disclosure are described in greater detail, it is to be understood that the applicator sets and methods are not limited to particular embodiments described, as such may, of course, vary. It is also to be understood that the terminology used herein is for the purpose of describing particular embodiments only, and is not intended to be limiting, since the scope of the applicator sets and methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the applicator sets and methods. The upper and lower limits of these smaller ranges may independently be included in the smaller ranges and are also encompassed within the applicator sets and methods, subject to any specifically excluded limit in the stated range. Where the stated range includes one or both of the limits, ranges excluding either or both of those included limits are also included in the applicator sets and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the applicator sets and methods belong. Although any applicator sets and methods similar or equivalent to those described herein can also be used in the practice or testing of the applicator sets and methods, representative illustrative applicator sets, methods and materials are now described.

All publications and patents cited in this specification are herein incorporated by reference as if each individual publication or patent were specifically and individually indicated to be incorporated by reference and are incorporated herein by reference to disclose and describe the applicator sets, methods and/or materials in connection with which the publications are cited. The citation of any publication is for its disclosure prior to the filing date and should not be construed as an admission that the present applicator sets and methods are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the applicator sets and methods, which are, for clarity, described in the context of separate embodiments, may also be provided in combination in a single embodiment. Conversely, various features of the applicator sets and methods, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present applicator sets and methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present applicator sets and methods. Any recited method can be carried out in the order of events recited or in any other order which is logically possible.

In further describing embodiments of the present disclosure, aspects of embodiments of the subject applicator sets will be described first in greater detail. Thereafter, aspects of embodiments of the methods of using the applicator sets are described in greater detail.

Sensor Applicator Sets

An issue with conventional in vivo analyte monitoring systems designed to determine analyte concentration in interstitial fluid (ISF) of the subcutaneous space is that there is a substantial time lag that exists between the ISF analyte concentration and the blood analyte concentration. This is the case when the monitored analyte is glucose, and for other analytes whose concentration changes quickly. (Glucose will be used primarily as an exemplary analyte herein, but it is to be understood that other analytes may be monitored.) For example, a time lag in the distribution of glucose from blood to the interstitium has been observed. As a result of this lag, ISF glucose concentrations do not correlate exactly with blood glucose concentrations at a given point in time. The present inventors have surprisingly discovered that—as compared to traditional in vivo analyte monitoring systems which determine ISF analyte concentrations in subcutaneous tissue (e.g., 3 mm to 10 mm beneath the surface of the skin)—in vivo monitoring of dermal fluid (e.g., 0.5 mm to 3 mm) analyte concentration provides analyte concentration data with markedly reduced lag times as compared to blood analyte concentration (e.g., venous glucose). Accordingly, analyte concentration data obtained using a dermal analyte sensor correlates more closely to the analyte concentration in blood as compared to in vivo ISF sensors.

Despite the above-mentioned discovery of the advantages afforded by measuring analyte concentrations in dermal fluid, significant technical hurdles exist with respect to the insertion of one or more sensor components, e.g., a working electrode, into and no deeper than a dermal layer of a subject. For example, the significantly reduced scale of the sensor component(s) necessary for a dermal sensor as compared to an ISF/subcutaneous sensor renders the dermal sensing components extremely fragile and therefore more susceptible to breaking under the modest forces exerted on the sensor by the skin surface and/or underlying tissue as the sensor is being inserted.

As such, monitoring the concentration of an analyte in the dermal layer of a subject requires more than simply scaling down the size of an ISF/subcutaneous analyte sensor. New strategies for inserting components of a dermal analyte sensor are needed, and are therefore provided in the present disclosure. Technical challenges of sensors sized for dermal sensing are also significant. For example, sensors must be sized so that they are only positionable in the dermal layer, but must also be able to provide acceptable current densities, stabilities, and sensitivities, in addition to being manufacturable with any consistency and reliability, e.g., by high speed manufacturing techniques. These challenges are met by the devices and methods of the present disclosure.

The present disclosure provides various embodiments of dermal sensors, sensor applicator sets, and methods of using and making the same. Detecting the presence and/or concentration of a dermally-positioned sensor is also provided, where the detection step is carried out using an electrochemical measurement technique. For example, a dermal sensor may detect current or may employ potentiometry. According to certain embodiments, an analyte-associated signal obtained from a dermally-positioned sensor is detected by an electrochemical measurement technique including, but not limited to, amperometry, coulometry, voltammetry, and potentiometry. Dermal sensors may also provide analyte information using optical or colorimetric means.

A sensor applicator set is a collection of elements including a dermal in vivo analyte sensor readied for dermal positioning (at least a sensing region of a working electrode), and an insertion needle that positions the dermal sensor only in the dermal layer of a subject. Other sensor electrodes may be included for dermal positioning or may be positioned remotely from the dermal area in which the working electrode is positioned, e.g., may be positioned outside a subject's body. For example, other than a working electrode and particularly a sensing region of a working electrode, additional sensor components may be included such as one or a second working electrode, a counter electrode, reference electrode, or a counter/reference electrode. The present disclosure of inserting a dermal sensor in a dermal space contemplates all of these various embodiments unless specifically noted and at least includes dermally positioning at least a sensing region of a working electrode of a sensor. The in vivo analyte sensors designed specifically for dermal positioning are referred to herein as a sensor, dermal sensor, analyte sensor, in vivo sensor, and the like.

As will be described below, the embodiments disclosed herein can also be configured and used such that the sensor and/or insertion needle extend beyond the dermal layer and into the subcutaneous layer. The present disclosure of inserting a sensor into or through subcutaneous tissue contemplates all variations of electrode positioning unless specifically noted and at least includes positioning at least a sensing region of a working electrode of a sensor into the subcutaneous tissue. Additional sensor components may be included such as one or a second working electrode, a counter electrode, reference electrode, or a counter/reference electrode, and each of these may be positioned in the subcutaneous tissue, the dermal tissue, or any combination thereof, when the sensing region of the working electrode is in either the dermal layer or the subcutaneous layer.

In addition to a dermal sensor and sensor insertion needle, the collection of sensor applicator elements optionally includes one or more elements for mounting and/or fixing the sensor and insertion needle at a desired distance and/or orientation (e.g., angle) relative to a reference point such as each other before, during, or after the sensing region of the working electrode is inserted at the dermal layer. Other optional elements, such as elements that facilitate manually driven or non-manually driven (e.g., automatically) or semi-manually driven insertion of the sensor and/or insertion needle may be included. The subject sensor applicator sets may include elements in addition to the dermal sensor and insertion needle that insert a sensing portion of a working electrode in a dermal area, as well as removing one or more elements (e.g., the insertion needle) of the applicator set before, during, or after the sensing region of the working electrode is inserted at the dermal layer.

The dermal insertion needle is configured to create an insertion path at a skin site of a subject to place a sensor in the dermal layer and no further. The dermal sensor is inserted into the insertion path and at the dermal layer, but not through a dermal layer. In certain aspects, during operation of the applicator set, the insertion needle creates an insertion path for the sensor before the insertion of the sensor into, but not through, a dermal layer is initiated. In other words, an insertion sequence in an embodiment includes inserting the insertion needle to the dermal layer to first form a path into the dermal layer, and then inserting a dermal sensor in the formed path to and into the dermal layer, where advancing the dermal sensor in the formed path may occur before the insertion needle is removed from the formed path or after the insertion needle is removed. For example, an insertion needle may be inserted (e.g., manually or automatically) at a skin site to a desired dermal depth to create a suitable insertion path for the sensor in the dermal layer. Upon removal of the insertion needle from the dermal layer, the sensor is then inserted (e.g., manually or automatically using mechanical components) into the insertion path, but not through a dermal layer at the skin site of the subject.

In other aspects, during operation of the applicator set, the insertion needle creates an insertion path for the sensor as the sensor is being inserted into but not through a dermal layer at the skin site of the subject. That is, the insertion needle and the sensor move together and are simultaneously inserted into the skin of the subject, where the insertion needle and sensor are in an orientation relative to each other such that the insertion needle creates an insertion path through which the sensor travels as the insertion needle and sensor pass through the skin surface together and to a desired dermal depth. A dermal sensor may follow, but trail, an insertion needle through a needle-formed insertion path to the dermal layer.

Due to the small scale of the dermal sensors and the need for creating a similarly small scaled insertion path for the sensor in the dermal layer, the conventional methodology of positioning the sensor within a lumen of an insertion needle is not possible. In particular, positioning of the sensor within the lumen of the needle requires that the needle is sufficiently large to house the sensor resulting in a needle having a relatively larger diameter than the sensor thereby creating a wider insertion path than the width of the dermal sensor. Since the dermal sensor is to be positioned in the dermal layer of the skin, having an insertion path that is significantly wider than the width of than the sensor increases the possibility of instability of the positioned sensor, irritation at the insertion site, damage to surrounding tissue, and breakage of capillary blood vessels resulting in fouling of the dermal fluid with blood.

Likewise, positioning a dermal sensor in an adjacent side-by-side arrangement with its insertion needle also creates an undesirable result, including an insertion path that is too wide. This arrangement creates an insertion path at the surface of the skin that is adjacent to—and different from— the location at which the sensor would come into contact with the surface of the skin. The disadvantage of this arrangement in which the needle and sensor are parallel to each other and are both at a normal angle relative to the skin is exemplified in Panel A of FIG. 1. In particular, Panel A of FIG. 1 shows sensor applicator set 100 that includes base 101 that holds dermal sensor 102 and insertion dermal insertion needle 104. Proximal region 106 of sensor 102 and proximal region 108 of insertion needle 104 are next to each other and are in parallel orientation with respect to each other, i.e., are not converging towards each other. Sensor 102 and needle 104 also include distal regions 107 and 109, respectively. Proximal and distal are relative terms defined by a spatial relationship between elements in comparison to the point of reference of the base of an applicator set such that sensor proximal region 106 is closer to base 101 than sensor distal region 107. The longest axis Ln of insertion needle 104 is disposed parallel to the longest axis Ls of sensor 102, and as shown are parallel to each other and do not converge towards each other. In this parallel and non-converging orientation, inserting the applicator set into the subject results in the application of forces at two different locations on the skin surface—indicated by lines 103 and 105 at the sensor distal region 107 and the insertion needle distal region 109. Therefore, this system would not allow for co-localizing the point at which the insertion needle 104 and sensor 102 contact the surface of the skin. In fact, it provides for two different contact points 103 and 105 as exemplified in Panel A of FIG. 1.

In contrast, the present inventors have discovered that by angling the sensor and/or insertion needle relative to a reference point enables co-localization of the tip of the insertion needle and the tip of the sensor and creates a single contact point at the surface of the skin. As such, the insertion needle creates a leading edge at the surface of the skin to form an insertion path into the dermal layer for the sensor as the sensor is inserted into a subject. The insertion needle and/or dermal sensor may be angled relative to a reference point (e.g., each other, surface of the skin, or the base of the applicator set) for insertion, where the angle of the needle differs from the angle of the sensor. For example, the reference point may be the skin surface to be breached for dermal insertion, or may be a reference or component of the sensor applicator set. In some embodiments, the needle may be disposed at an angle relative to the sensor. For example, when designed so that the needle is angled relative to the sensor, the needle creates a leading edge for the sensor during operation of the applicator set.

This discovery is schematically illustrated in FIG. 1, panel B. An applicator set according to embodiments of the present disclosure is schematically illustrated in FIG. 1, Panel B. In these embodiments, the sensor and/or needle are angled relative to a reference point. For example, one of the sensor or insertion needle may be angled relative to the other, or one or both may be angled relative to a skin surface or another element of the applicator set. The angles of each may differ and the needle may be angled a first angle and the sensor may be angled a second angle. As shown in FIG. 1, panel B, applicator set 110 includes base 111 that holds sensor 112 and insertion needle 114 in an orientation so that they are not spaced apart a uniform distance from each other, but rather have a varying, i.e., changing, distance between them so that needle 114 converges towards sensor 112 to come close to, and in certain embodiments physically contacts, sensor 112. Sensor proximal region 116 and needle proximal region 118 are spaced apart at their proximal regions, but are close to each other or are in contact with each other at converging region C to provide an angle 120 between the sensor and needle. Angle 120 can range from 5° to 20°, where in some embodiments angle 120 ranges from 5° to 17° or 7° to 15° or 9° to 13°, e.g., 9°, 10°, 11°, 12°, or 13°.

The longest axis $Ln_1$ of insertion needle 114 and the longest axis $Ls_1$ converge towards each other. In converging region C, the insertion needle and the dermal sensor come close to or contact each other at locations distal to proximal portions 116 and 118, respectively. In this particular example shown in FIG. 1, panel B, the insertion needle is longer than the dermal sensor, and a non-terminal (or "body") portion (i.e., an intermediate region 121) of the insertion needle comes close to (the terminal end of the convergence) or contacts the dermal sensor at the sensor distal end 117, but not at the sensor proximal end which remains spaced apart from the needle. However, variations are possible, e.g., such as selecting a length and/or angle of the insertion needle such that the needle and sensor come close to each other and in some embodiments contact each other at or near the distal ends of both the needle and sensor.

In any event, as a result of the insertion needle being disposed at angle 120 relative to the dermal sensor, and upon insertion of the needle and sensor into a subject, the insertion needle creates an insertion path for the sensor such that forces acting upon the dermal sensor from a tissue surface or underlying tissue of the subject during insertion are eliminated or reduced as compared to the forces acting upon a sensor in the applicator set configuration shown in FIG. 1, Panel A. That is, when the insertion needle is angled relative to the dermal sensor to contact (or come close to contacting) the sensor at a portion of the dermal sensor (e.g., at or near the distal end of the sensor), it is not required that the sensor form its own insertion path through the tissue surface and/or underlying tissue of the subject. Rather, the forces applied by the tissue surface or underlying tissue during insertion are primarily applied to and absorbed by the insertion needle—indicated by line 115 at the tip of insertion needle 114. In addition, by contacting the dermal sensor in the embodiments in which the needle physically contacts the sensor, the insertion needle can also assist in stabilizing the sensor by counteracting forces applied by the tissue of the subject to the sensor in the direction of the insertion needle. In this way, the portion of the dermal sensor inserted into the dermal layer (i.e., the insertion length or sensing portion of the sensor) can have a length of 0.5 mm to 3 mm, or even 1 mm to 2 mm, and can be inserted through the skin and into (and not through) a dermal layer of a subject and used to determine analyte levels of a dermal fluid without damage to the sensor.

An insertion needle may be disposed at an angle relative to the applicator base such that the needle is not at a 90° right angle relative to the base, but that it is positioned at an acute angle (e.g., 1° to 89°) relative to the base and angled in the direction towards the dermal sensor of the base, as exemplified in FIG. 1, panel B. For example, the angle of the needle 114 can also be described by the relationship of the needle to the base 111 to which it is held. Panel B of FIG. 1 shows angle 122 between axis $Ln_1$ of needle 110 and base 111. Angle 122 is an acute angle resulting in angling the distal end of the needle in the direction of the sensor. Angle 122 can range from 65° to 85°, including 70°, 75°, or 80°.

The angle of a sensor can also be described by the relationship pf the sensor to the base 11 to which it is held. As shown in FIG. 1 Panel B, axis $Ls_1$ of the dermal sensor is disposed at angle 123 relative to the base, where in this embodiment angle 123 is a perpendicular angle (i.e., 90°) between the sensor and the base, and the sensor is therefore also at a 90° angle relative to the skin surface into which it is inserted if inserted with axis $Ls_1$ normal to the skin. Accordingly, as shown in panel B of FIG. 1, embodiments include longitudinal axis $Ln_1$ of the insertion needle disposed at an acute angle 122 relative to the base and axis $Ln_1$ and the longest axis of the sensor $Ls_1$ converge towards each other at area C. While angle 123 is shown in Panel B as a 90° angle, it can be anywhere from 80°-100°.

In certain embodiments, a needle and sensor are parallel to each other and both are at a non-normal angle relative to the skin.

The insertion needle is dimensioned such that the applicator set provides for insertion of at least a portion of the dermal sensor into the dermal layer, but not through the dermal layer of the skin. According to certain embodiments, the insertion needle has a cross sectional diameter (width) of from 0.1 mm to 0.5 mm. For example, the insertion needle may have a diameter of from 0.1 mm to 0.3 mm, such as from 0.15 mm to 0.25 mm e.g., 0.16 mm to 0.22 mm in diameter. A given needle may have a constant, i.e., uniform, width along its entire length, or may have a varying, i.e., changing, width along at least a portion of its length, such as the tip portion used to pierce the surface of the skin.

An insertion needle has a length to insert a dermal sensor just into the dermal layer, and no more. Insertion depth may be controlled by the length of the needle and/or configuration of the base other applicator components that limit insertion depth.

An insertion needle may have a length of from 1.5 mm to 25 mm. For example, the insertion needle may have a length of from 1 mm to 3 mm, from 3 mm to 5 mm, from 5 mm to 7 mm, from 7 mm to 9 mm, from 9 mm to 11 mm, from 11 mm to 13 mm, from 13 mm to 15 mm, from 15 mm to 17 mm, from 17 mm to 19 mm, from 19 mm to 21 mm, from 21 mm to 23 mm, from 23 mm to 25 mm, or a length greater than 25 mm. It will be appreciated that while an insertion needle may have a length up to 25 mm, in certain embodiments the full length of the needle is not inserted into the subject because it would extend beyond the dermal space. Non inserted needle length may provide for handling and manipulation of the needle in an applicator set. Therefore, while an insertion needle may have a length up to 25 mm, the insertion depth of the needle in the skin on a subject in those certain embodiments will be limited to the dermal layer, e.g., about 1.5 mm to 4 mm, depending on the skin location, as described in greater detail below. However, in all of the embodiments disclosed herein, the insertion needle can be configured to extend beyond the dermal space, such as into (or even fully through) subcutaneous tissue (e.g., 3 mm to 10 mm beneath the surface of the skin depending on the location of the skin on the body). Any of the insertion needles described herein may be solid insertion needles, where by "solid" is meant that the needles do not have an internal space and/or lumen (e.g., are not hollow), or they may include an internal space or lumen. An insertion needle of the subject applicator sets may be bladed or non-bladed.

Likewise, in certain embodiments, a dermal sensor is sized so that at least a portion of the sensor is positioned in the dermal layer and no more, and a portion extends outside the skin in the transcutaneously positioned embodiments. That is, a dermal sensor is dimensioned such that when the dermal sensor is entirely or substantially entirely inserted into the dermal layer, the distal-most portion of the sensor (the insertion portion or insertion length) is positioned within the dermis of the subject and no portion of the sensor is inserted beyond a dermal layer of the subject when the sensor is operably dermally positioned.

The dimensions (e.g., the length) of the sensor may be selected according to the body site of the subject in which the sensor is to be inserted, as the depth and thickness of the epidermis and dermis exhibit a degree of variability depending on skin location. For example, the epidermis is only about 0.05 mm thick on the eyelids, but about 1.5 mm thick on the palms and the soles of the feet. The dermis is the thickest of the three layers of skin and ranges from about 1.5 mm to 4 mm thick, depending on the skin location. For implantation of the distal end of the sensor into, but not through, the dermal layer of the subject, the length of the inserted portion of the dermal sensor should be greater than the thickness of the epidermis, but should not exceed the combined thickness of the epidermis and dermis. Methods may include determining an insertion site on a body of a user and determining the depth of the dermal layer at the site, and selecting the appropriately-sized applicator set for the site.

In certain aspects, the sensor is an elongate sensor having a longest dimension (or "length") of from 0.25 mm to 4 mm. The length of the sensor that is inserted, in the embodiments in which only a portion of a sensor is dermally inserted, ranges from 0.5 mm to 3 mm, such as from 1 mm to 2 mm, e.g., 1.5 mm. The dimensions of the sensor may also be expressed in terms of its aspect ratio. In certain embodiments, a dermal sensor has an aspect ratio of length to width (diameter) of about 30:1 to about 6:1. For example, the aspect ratio may be from about 25:1 to about 10:1, including 20:1 and 15:1. The inserted portion of a dermal sensor has sensing chemistry.

However, all of the embodiments disclosed herein can be configured such that at least a portion of the sensor is positioned beyond the dermal layer, such as into (or through) the subcutaneous tissue (or fat). For example, the sensor can be dimensioned such that when the sensor is entirely or substantially entirely inserted into the body, the distal-most portion of the sensor (the insertion portion or insertion length) is positioned within the subcutaneous tissue (beyond the dermis of the subject) and no portion of the sensor is inserted beyond the subcutaneous tissue of the subject when the sensor is operably positioned. As mentioned, the subcutaneous tissue is typically present in the region that is 3 mm to 10 mm beneath the outer skin surface, depending on the location of the skin on the body.

For implantation of the distal end of the sensor into, but not through, the subcutaneous tissue of the subject, the length of the inserted portion of the sensor should be greater than the thickness of the epidermis and dermis, but should not exceed the combined thickness of the epidermis, dermis, and subcutaneous tissue (when inserted at a normal angle to the skin surface—a non-normal angle allows an insertion portion of the sensor that can exceed these combined thicknesses since the absolute depth of penetration is less than the length of the inserted portion of the sensor). For example, the length of the sensor that is inserted can be greater than 3 mm, or any length that places the sensing region of the working electrode into the subcutaneous tissue, further taking into account insertion of the sensor at a non-normal angle to the skin surface (e.g., 70 degrees), which will require a longer sensor. In all embodiments, the sensor can be configured to extend beyond the subcutaneous tissue as well.

The subject applicator sets may include a sensor having one or more structural features that enhance the association of the sensor with the insertion needle and/or facilitates the disposition of the insertion needle at the desired angle relative to the sensor. In certain aspects, a distal end of the sensor includes a groove that is complementary (e.g., in a male-female-type relationship) to the exterior shape and dimensions of the insertion needle (or vice versa). The groove may have a shape and dimension complementary to an exterior area of the insertion needle (see, e.g., grooves 411 and 611 in FIG. 4, Panel A and FIG. 6, Panel A, respectively) such as a distal end portion of the insertion needle. In embodiments where the sensor has a groove having a shape complementary to the insertion needle, the groove may have an angle that corresponds to the angle of the insertion needle (e.g., angle 120 of FIG. 1, panel B). In this way, the insertion needle may be supported or stabilized at the desired angle by the grooved portion of the sensor. In other aspects, the distal end of the sensor does not have a groove complementary to the insertion needle, but rather has an angle (e.g., a flat, angled surface) that corresponds to the desired angle of the insertion needle. The angled portion of the distal end of the sensor may perform the same or similar function as the aforementioned groove, in that the insertion needle may be supported or stabilized at the desired angle by the angled portion at the distal end of the sensor.

According to certain embodiments, the subject devices and applicator sets include a sensor that is a microprojection having a solid microneedle-like structure without a central bore (or lumen) through which liquid is injected or withdrawn. Suitable microprojections may be obtained, e.g., by singulating individual microprojections from a plurality of microprojections present on a roll or other sensor upon which a plurality of microprojections is disposed.

Sensors of the subject applicator sets may be made of a conductive material and an insulative material that is non-conductive, semiconductive, or conductive. In certain embodiments, the sensor is made of a nonconductive or conductive plastic. For example, the sensor may be a non-conductive plastic microprojection upon which one or more layers of conductive material are disposed (e.g., one, two, or more conductive layers may be disposed on the plastic microprojection). The one or more layers of conductive material may serve as the working electrode. Additional layers may be disposed on the one or more conductive layers, such as a sensing layer (e.g., a layer that includes an analyte-responsive enzyme, and may also include a redox mediator, or both), a mass transport limiting layer that limits access of certain chemical species (e.g., the analyte, an interfering component, or the like) to a sensing layer, and/or any other layer that may improve the performance or provide additional desired functionalities to the sensor.

Figure 2:
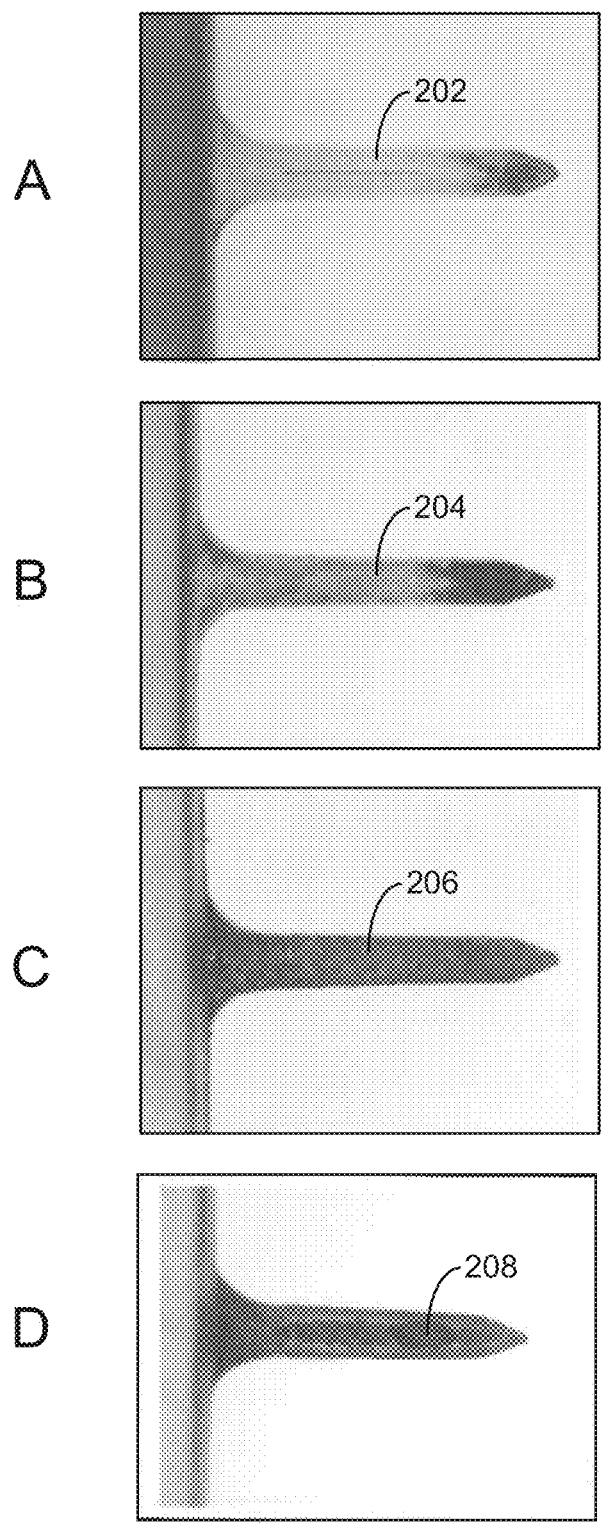
FIG. 2 shows the formation of a sensor in Panels A-D that include a working electrode according to one embodiment of the present disclosure.

The formation of a sensor that includes a working electrode according to one embodiment of the present disclosure is shown in FIG. 2. Panel A is an uncoated sensor, which in this example is a plastic microprojection 202 having a length of about 1.5 mm. The plastic microprojection may be coated (e.g., sputter coated) with a layer of conductive material (in this example, gold layer 204) to form a working electrode as shown in Panel B. The coated sensor may be further coated with an optional layer of a second material (in this example, carbon layer 206) as shown in Panel C. This second layer may be useful, e.g., to enhance electrode conductivity and/or adhesion of any additional layers (e.g., a sensing layer) to the electrode. In the embodiment of FIG. 2, the electrode includes sensing layer 208 that includes an analyte-responsive enzyme disposed on the second layer, as shown in Panel D. A redox mediator may also be included with the enzyme. Included as an outermost layer (not shown) in the embodiment of FIG. 2 is an analyte transport limiting layer.

A sensor of the subject applicator sets may be made of a conductive material which may exhibit sufficient conductivity to obviate any need for an additional conductive coating to provide a working electrode capable of electrochemical determination of the concentration of the analyte. According to certain aspects, the conductive material is a conductive plastic. The conductive plastic may include a polymer matrix (e.g., a non-conductive or substantially non-conductive polymer matrix) that includes a conductive material interspersed therein. The polymer matrix may include any polymer suitable for forming a conductive plastic, including but not limited to, a polyether block amide polymer. The conductive material may be a conductive material that confers sufficient conductivity to the polymer matrix. Such materials may include conductive particulate matter, such as conductive metal particles, microspheres coated with a conductive material, carbon, and/or the like. In certain aspects, the conductive material interspersed in the polymer matrix is carbon. When the conductive material interspersed within the polymer matrix is carbon, the carbon may be present in the polymer matrix in an amount ranging from 5% to 30% w/w. For example, the carbon may be present in the polymer matrix in an amount ranging from 7% to 20% w/w, such as from 8% to 12% w/w, e.g., 10% w/w.

Figure 3:
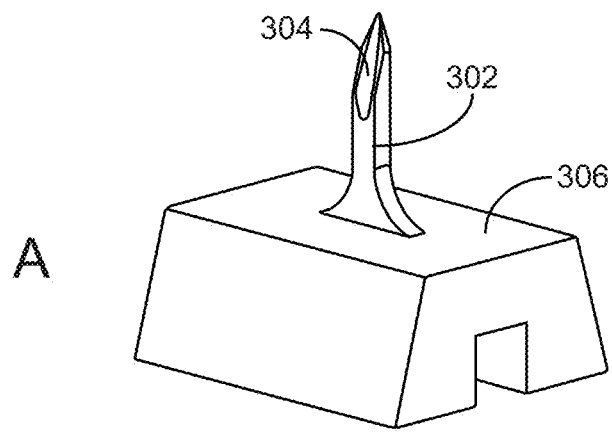
FIG. 3 schematically illustrates a sensor in Panels A-C according to one embodiment of the present disclosure.
Figure 3:
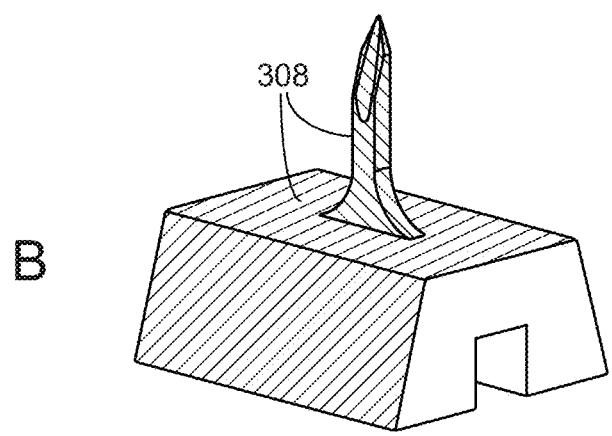
Figure 3:
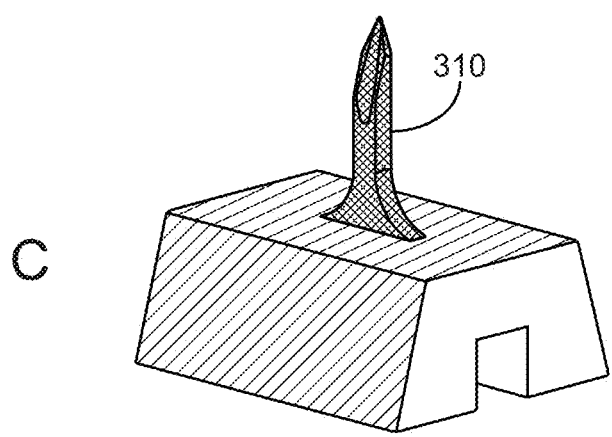

A sensor that can be used in an applicator set according to one embodiment of the present disclosure is schematically illustrated in FIG. 3. As shown in Panel A, the sensor includes substrate 302 having groove 304, with the sensor positioned on base 306. In this example, the substrate and base are made of plastic. To form a working electrode, all or a portion of the substrate (and optionally one or more surfaces of the base) is coated with a conductive layer (e.g., Au layer 308) by sputter coating or any other suitable approach for providing a conductive layer on a plastic substrate (Panel B). Additional layers may be applied to the substrate and/or base, such as carbon layer 310 disposed on the Au-coated substrate (e.g., by dip coating, spraying or submersion), as shown in Panel C. A sensing layer, a protective and/or mass transport limiting layer, and/or the like may further be provided on carbon layer 310 to enhance the performance of and/or provide additional functionalities to the sensor.

Figure 4:
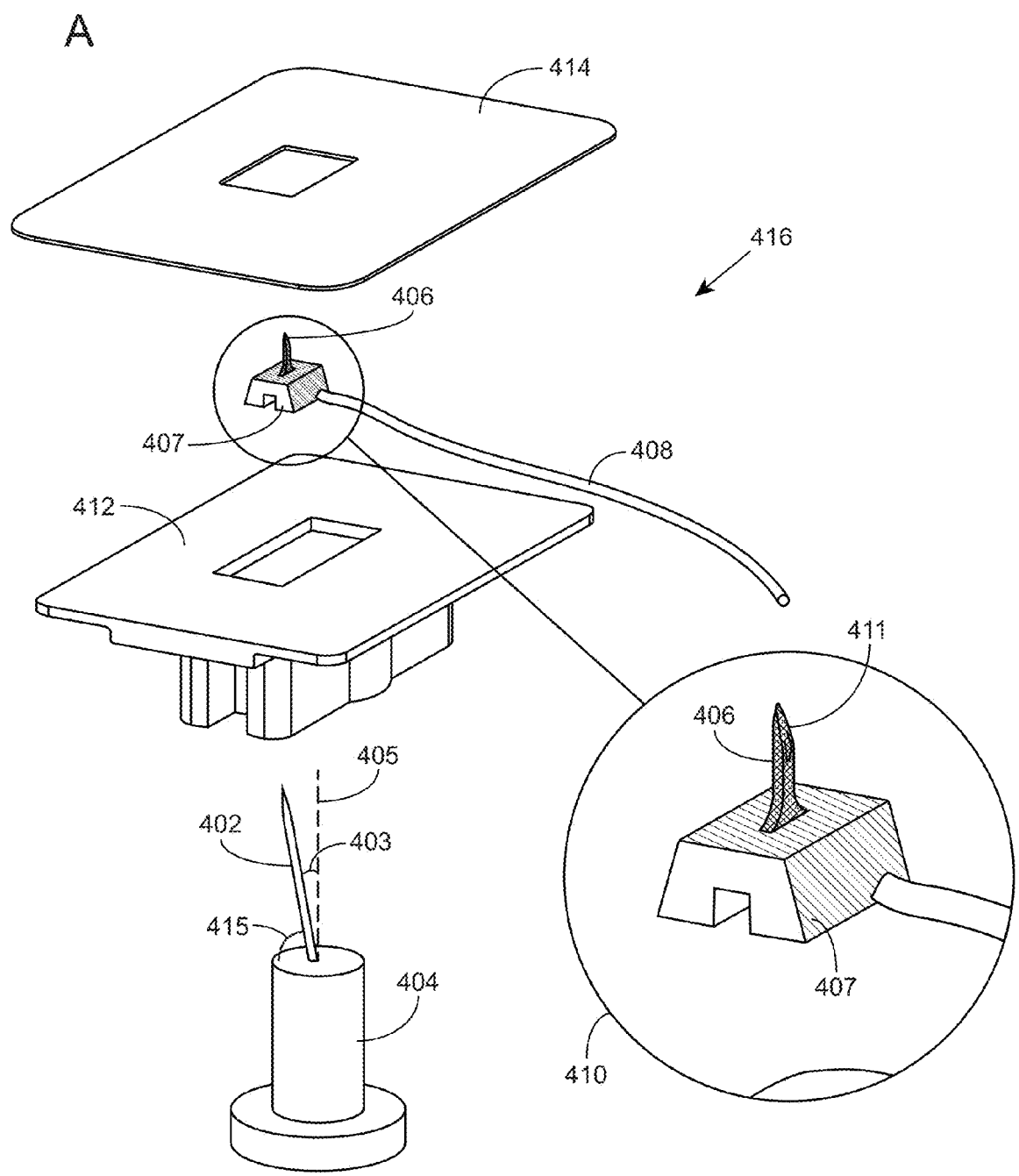
FIG. 4 schematically illustrates a sensor applicator set in Panels A-C according to one embodiment of the present disclosure.
Figure 4:
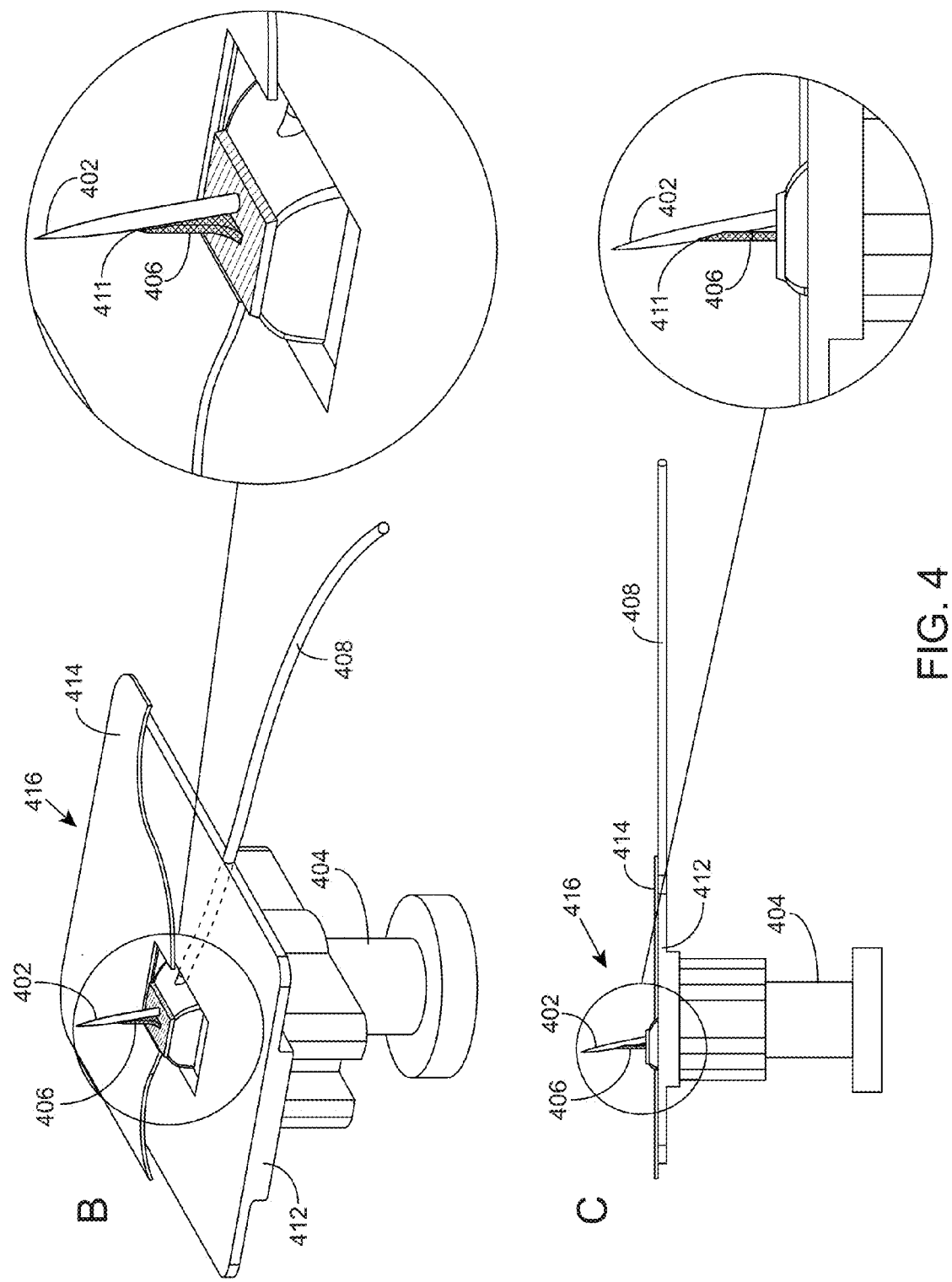

Various components of a disassembled sensor applicator set 416 according to one embodiment of the present disclosure are shown in FIG. 4, Panel A. The proximal end of insertion needle 402 is disposed within or on molded hub 404. Insertion needle 402 is disposed at an angle 403 (such as between 9° and 13°, e.g., 11°) relative to vertical axis 405 extending from the top surface of molded hub 404, and/or angle 415 may also be formed similar to angle 122 of Panel B of FIG. 1. According to this embodiment, the applicator set includes dermal sensor 406 having an appropriate size, shape, and dimension for insertion into a dermal layer of a subject and for generating analyte-responsive signals in response to analyte present in the dermal fluid. Sensor 406 may be the same as, similar to, or different from the sensor shown in FIG. 3, Panel C. Wire 408 is connected to a conductive coating on the base 407 of sensor 406 and facilitates electrical communication between sensor 406 and components of an analyte sensing system, e.g., a voltage source, control electronics, and/or the like. View 410 is a magnified view of sensor 406 and wire 408 connected thereto. As can be seen in view 410, dermal sensor 406 includes groove 411 having a shape and angle complementary to a portion of insertion needle 402. In this embodiment, the applicator set includes assembly mount 412 for mounting/fixing the sensor and insertion needle in the desired position relative to each other, as well as adhesive 414 for securing the dermal sensor in its final position upon insertion into the subject.

Assembled sensor applicator set 416, which includes dermal sensor 406 and insertion needle 402 disposed at an angle relative to sensor 406, is shown in FIG. 4, Panel B (left). Adhesive 414 is cut-away to show the other elements of applicator set 416, and a magnified view of the sensor and insertion needle associated with each other via their complementary shapes is also shown in FIG. 4, Panel B. A side view of assembled applicator set 416 is provided in FIG. 4, Panel C, including a magnified side view of dermal sensor 406 and insertion needle 402 on the right.

Figure 5:
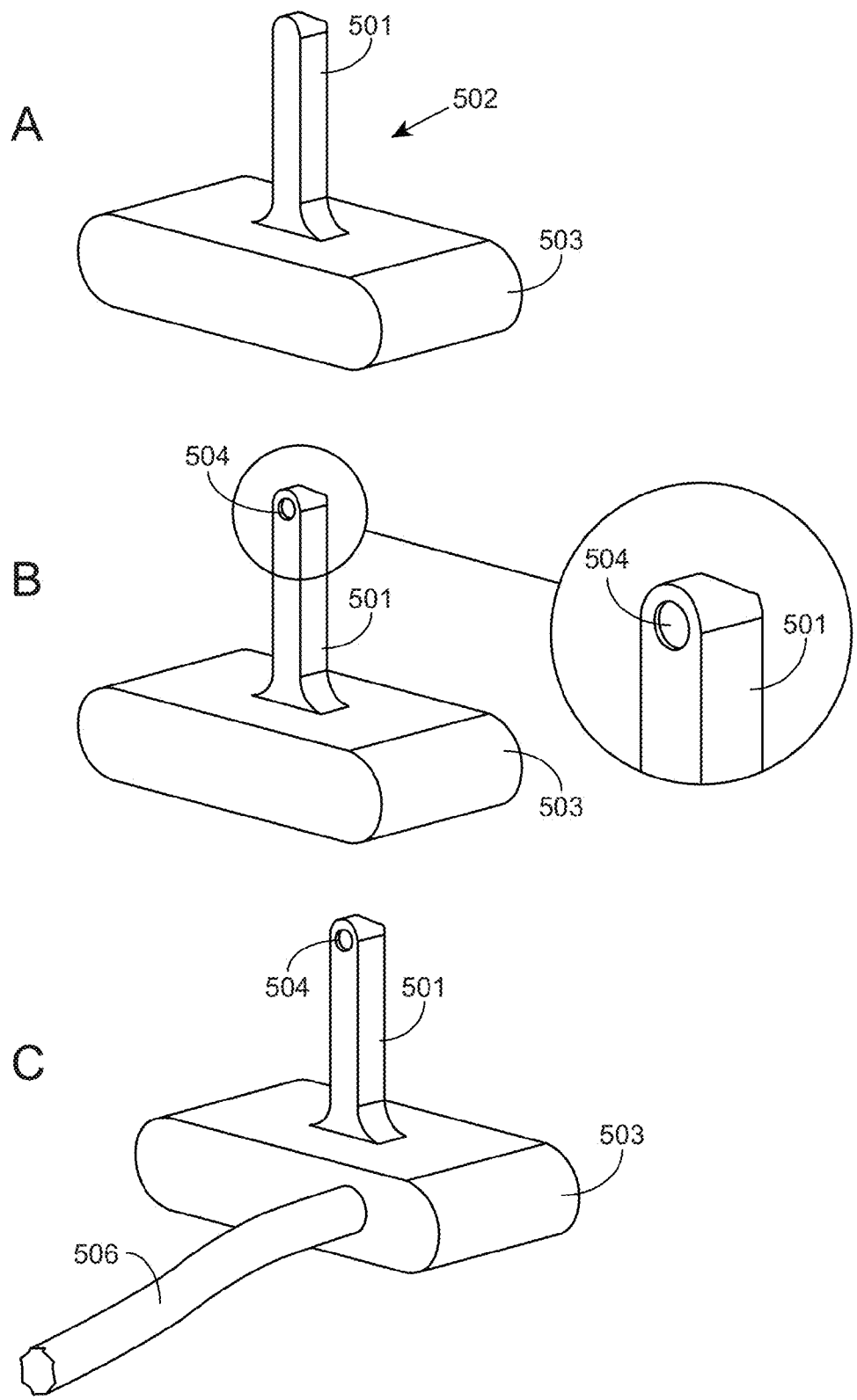
FIG. 5 schematically illustrates a sensor in Panels A-C according to one embodiment of the present disclosure.

As described above, according to certain embodiments, applicator sets of the present disclosure may include a dermal sensor molded (e.g., by injection molding) from a nonconductive or conductive plastic. An exemplary applicator set 502 according to this embodiment is shown in FIG. 5. Dermal sensor 501 and base 503, e.g., molded from conductive plastic, is shown in FIG. 5, Panel A. The conductive plastic may include a polymer matrix (e.g., a polyether block amide polymer) having a conductive material (e.g., carbon particles) disposed therein, as described hereinabove. In certain aspects, a distal portion of the sensor 501 includes a divot. An exemplary divot 504 is shown in FIG. 5, Panel B. When a dermal sensor includes divot or through hole, sensing reagents or the like may be deposited therein. If the divot is to be used for deposition of sensing reagents therein, the area and/or volume of the divot may be selected during the manufacturing design process to provide one or more desired sensor characteristics (e.g., working electrode characteristics), such as a particular sensitivity in response to the analyte, e.g., where the sensitivity (e.g., analyte-responsive signal) may be increased or decreased by increasing or decreasing the area and/or volume of the recess, respectively. A dermal sensor may therefore include one or more structural features (e.g., a molded divot for deposition of sensor reagents, a molded groove having a shape complementary to the insertion needle, and/or the like) at one or more regions of the sensor. Electrical connecting wire 506 connected to the conductive plastic of the base is shown in FIG. 5, Panel C. The wire may be employed to facilitate electrical communication between sensor and base 502 and components of an analyte sensing system, e.g., a voltage source, control electronics, and/or the like.

Figure 6:
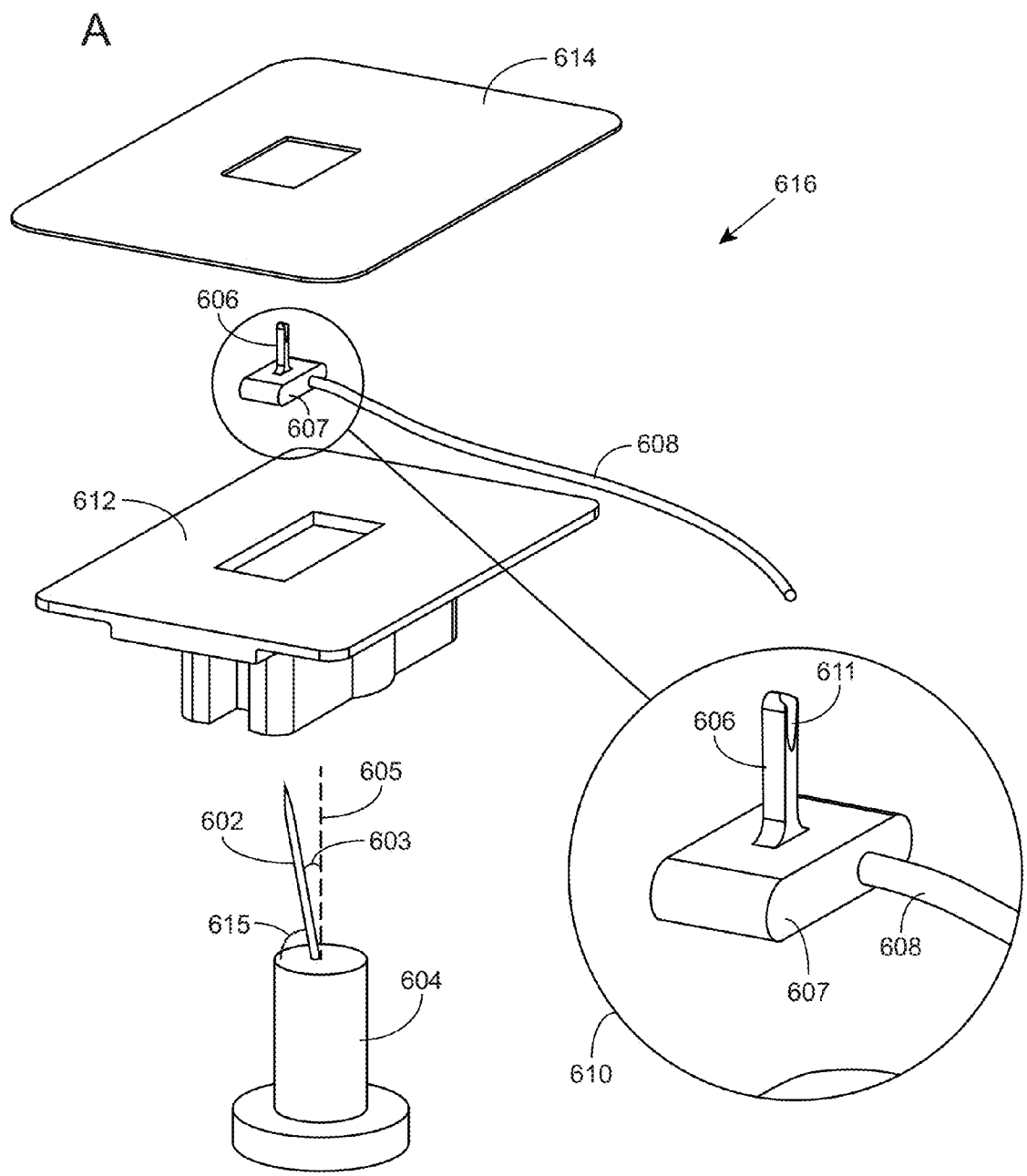
FIG. 6 schematically illustrates a sensor applicator set in Panels A-C according to one embodiment of the present disclosure.
Figure 6:
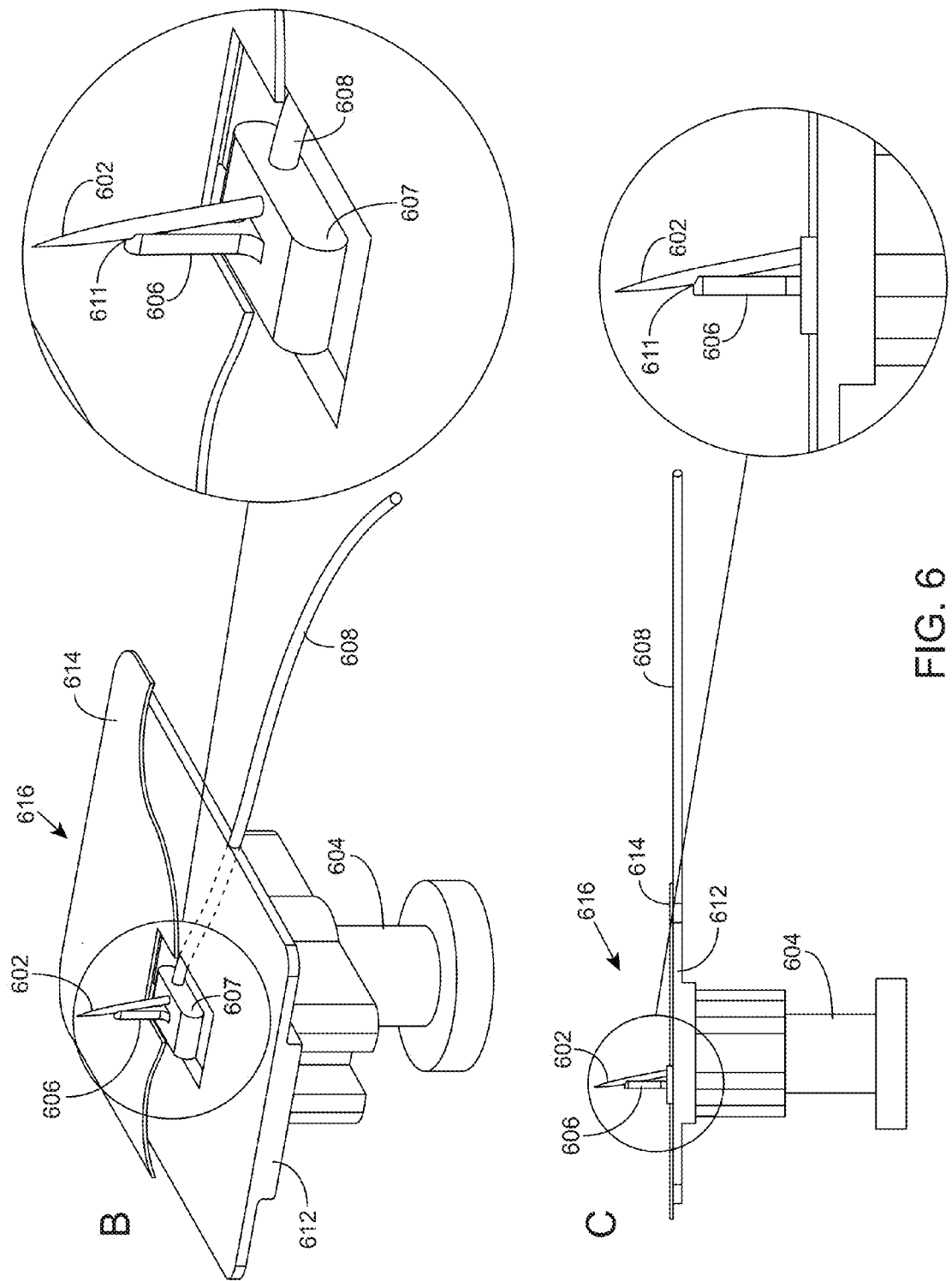

Components of a disassembled sensor applicator set 616 according to one embodiment of the present disclosure are shown in FIG. 6, Panel A. The proximal end of insertion needle 602 is disposed within or on hub 604. Insertion needle 602 is disposed at an angle 603 (such as between 9° and 13°, e.g., 11°) relative to vertical axis 605 extending from the top surface of molded hub 604, which may be its angle relative to the sensor upon assembly of the applicator set, and/or angle 615 may also be formed similar to angle 122 of Panel B of FIG. 1. According to this embodiment, the applicator set includes molded dermal sensor 606 and base 607 configured (e.g., sized, etc.) for insertion into a dermal layer of a subject and for generating analyte-responsive signals in response to analyte present in the dermal fluid. Molded dermal sensor 606 may be the same as, similar to, or different from the molded sensor shown in FIG. 5. Electrical connecting wire 608 is connected to the base 607 of molded sensor 606 and facilitates electrical communication between molded sensor 606 and components of an analyte sensing system, e.g., a voltage source, control electronics, and/or the like. View 610 is a magnified view of molded dermal sensor 606 and wire 608 connected thereto. As can best be seen in view 610, molded dermal sensor 606 includes a groove 611 having a shape and angle complementary to a body portion of insertion needle 602. In this embodiment, the applicator set includes assembly mount 612 for mounting/fixing the sensor and insertion needle in the desired position relative to each other, as well as adhesive 614 for securing the sensor in its final position upon insertion into the subject.

Assembled sensor applicator set 616, which includes dermal sensor 606 and insertion needle 602 disposed at an angle relative to sensor 606, is shown in FIG. 6, Panel B (left). Adhesive 614 is cut-away in FIG. 6, Panel B to show the other elements of applicator set 616. A magnified view of the dermal sensor and the insertion needle associated with each other via their complementary shapes is shown in FIG. 6, Panel B (right). A side view of assembled applicator set 616 is provided in FIG. 6, Panel C (left), including a magnified view of dermal sensor 606 and insertion needle 602 on the right.

Exemplary features and components of the sensors employed in the subject devices, applicator sets and methods are described in greater detail below. Any of the sensors and sensor applicator sets described above may include any such features and components, alone or in combination.

Conductive Material

As set forth above, in certain aspects, a dermal sensor employed by a subject applicator set is a dermal sensor that includes one or more conductive materials, e.g., in the form of conductive layers, integrated particles, and the like. The one or more conductive materials confer conductivity to the sensor, e.g., when the sensor includes a non-conductive or substantially non-conductive material (e.g., a non-conductive plastic material). For example, a conductive layer disposed on a non-conductive material may constitute the working electrode of the sensor. In certain aspects, a second conductive material, e.g., a conductive layer, electrically isolated from the first conductive material or layer, e.g., by an electrically insulating layer, may be added to provide a second electrode in addition to the working electrode (e.g., a counter or counter/reference electrode, a reference electrode, or the like).

A dermal sensor described herein may include one or more conductive layers made of a material independently selected from gold, carbon, platinum, ruthenium, palladium, silver, silver chloride, silver bromide, and combinations thereof. A conductive layer may be a layer of gold, tin oxide, platinum, ruthenium dioxide or palladium, indium tin oxide, zinc oxide, fluorine doped tin oxide, as well as other non-corroding materials known to those skilled in the art. The conductive layer can be a combination of two or more conductive materials. For example, the conductive layer may be constructed from a layer of gold on a first region of the sensor and a layer of carbon on a second region of the sensor.

The conductive layer may be applied to the sensor or a layer thereof by being deposited, such as by vapor deposition or vacuum deposition or otherwise sputtered, printed on a flat surface or in an embossed or otherwise recessed surface, transferred from a separate carrier or liner, etched, or molded. Suitable methods of printing include screen-printing, piezoelectric printing, ink jet printing, laser printing, photolithography, painting, gravure roll printing, transfer printing, and other known printing methods.

Sensing Layer

At least one or more working electrodes of a dermal sensor may include a sensing layer that includes sensing reagents to facilitate determination of a concentration of an analyte of interest. The sensing layer includes one or more components designed to facilitate the electrolysis of the analyte. The sensing layer may include, for example, an analyte responsive enzyme to catalyze a reaction of the analyte and produce a response at the working electrode, an electron transfer agent to indirectly or directly transfer electrons between the analyte and the working electrode, or both.

A variety of different sensing layer configurations may be used. In certain embodiments, the sensing layer is deposited on the conductive material of a working electrode. The sensing layer may extend beyond the conductive material of the working electrode. In some cases, the sensing layer may also extend over other electrodes, e.g., over a counter electrode and/or reference electrode (or counter/reference electrode). The sensing layer may be integral with the material of an electrode.

For example, a sensor for sensing glucose may include a first sensing layer which is spaced apart from the working electrode and contains a glucose-responsive enzyme, for example, glucose oxidase or glucose dehydrogenase. The reaction of glucose the presence of the appropriate enzyme forms hydrogen peroxide. A second sensing layer may be provided directly on the working electrode and contains a peroxidase enzyme and an electron transfer agent to generate a signal at the electrode in response to the hydrogen peroxide. The level of hydrogen peroxide indicated by the sensor then correlates to the level of glucose.

Another sensor which operates similarly can be made using a single sensing layer with both the glucose and the peroxidase being deposited in the single sensing layer.

A sensing layer that is in direct contact with the working electrode may contain an electron transfer agent to transfer electrons directly or indirectly between the analyte and the working electrode, and/or an enzyme to facilitate a reaction of the analyte. For example, a glucose, or oxygen electrode may be formed having a sensing layer which contains an enzyme, such as glucose oxidase, and an electron transfer agent that facilitates the electro-oxidation of the glucose.

In other embodiments the sensing layer is not deposited directly on the working electrode. Instead, the sensing layer may be spaced apart from the working electrode, and separated from the working electrode, e.g., by a separation layer. A separation layer may include one or more membranes or films or a physical distance. In addition to separating the working electrode from the sensing layer the separation layer may also act as a mass transport limiting layer and/or an interferent eliminating layer and/or a biocompatible layer.

In certain embodiments which include more than one working electrode, one or more of the working electrodes do not have a corresponding sensing layer, or have a sensing layer which does not contain one or more components (e.g., an electron transfer agent and/or enzyme) needed to electrolyze the analyte. Thus, the signal at this working electrode corresponds to background signal which may be removed from the analyte signal obtained from one or more other working electrodes that are associated with fully-functional sensing layers by, for example, subtracting the signal.

In certain embodiments, electron transfer agents have structures or charges which prevent or substantially reduce the diffusional loss of the electron transfer agent during the period of time that the sample is being analyzed. For example, electron transfer agents include but are not limited to a redox species, e.g., bound to a polymer which can in turn be disposed on or near the working electrode. The bond between the redox species and the polymer may be covalent, coordinative, or ionic. Although any organic, organometallic, or inorganic redox species may be bound to a polymer and used as an electron transfer agent, in certain embodiments the redox species is a transition metal compound or complex, e.g., osmium, ruthenium, iron, and cobalt compounds or complexes. Redox species described for use with a polymeric component may also be used without a polymeric component.

A type of polymeric electron transfer agent that may be used with the dermal sensors contains a redox species covalently bound in a polymeric composition, as described, e.g., in U.S. Pat. Nos. 6,605,200 and 6,605,201, the disclosures of which are incorporated herein by reference in their entireties for all purposes. An example of this type of mediator is poly(vinylferrocene). Another type of electron transfer agent contains an ionically-bound redox species. This type of mediator may include a charged polymer coupled to an oppositely charged redox species. Examples of this type of mediator include a negatively charged polymer coupled to a positively charged redox species such as an osmium or ruthenium polypyridyl cation. Another example of an ionically-bound mediator is a positively charged polymer such as quaternized poly(4-vinyl pyridine) or poly (1-vinyl imidazole) coupled to a negatively charged redox species such as ferricyanide or ferrocyanide. In other embodiments, electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

Suitable electron transfer agents are osmium transition metal complexes with one or more ligands, each ligand having a nitrogen-containing heterocycle such as 2,2'-bipyridine, 1,10-phenanthroline, 1-methyl, 2-pyridyl biimidazole, or derivatives thereof. The electron transfer agents may also have one or more ligands covalently bound in a polymer, each ligand having at least one nitrogen-containing heterocycle, such as pyridine, imidazole, or derivatives thereof. An example of an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Some derivatives of 2,2'-bipyridine for complexation with the osmium cation include but are not limited to 4,4'-dimethyl-2,2'-bipyridine and mono-, di-, and polyalkoxy-2,2'-bipyridines, such as 4,4'-dimethoxy-2,2'-bipyridine. Derivatives of 1,10-phenanthroline for complexation with the osmium cation include but are not limited to 4,7-dimethyl-1,10-phenanthroline and mono, di-, and polyalkoxy-1,10-phenanthrolines, such as 4,7-dimethoxy-1,10-phenanthroline. Polymers for complexation with the osmium cation include but are not limited to polymers and copolymers of poly(1-vinylimidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole, e.g., electron transfer agents with osmium complexed to a polymer or copolymer of poly(1-vinyl imidazole).

Embodiments may employ electron transfer agents having a redox potential ranging from about −200 mV to about +200 mV versus the standard calomel electrode (SCE). The sensing layer may also include an enzyme which is capable of catalyzing a reaction of the analyte. The enzyme may also, in some embodiments, act as an electron transfer agent. One example of a suitable enzyme is an enzyme which catalyzes a reaction of the analyte. For example, an enzyme, such as a glucose oxidase, glucose dehydrogenase (e.g., pyrroloquinoline quinone (PQQ) dependent glucose dehydrogenase, flavine adenine dinucleotide (FAD) dependent glucose dehydrogenase, or nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

In certain embodiments, an enzyme may be attached to a polymer, cross linking the enzyme with another electron transfer agent (which, as described above, may be polymeric). A second enzyme may also be used in certain embodiments. This second enzyme may be used to catalyze a reaction of a product compound resulting from the catalyzed reaction of the analyte. The second enzyme may operate with an electron transfer agent to electrolyze the product compound to generate a signal at the working electrode. Alternatively, a second enzyme may be provided in an interferent-eliminating layer to catalyze reactions that remove interferents.

Certain embodiments include a sensing layer that works at a gentle oxidizing potential, e.g., a potential of about +40 mV. This sensing layer uses an osmium (Os)-based mediator designed for low potential operation and is stably anchored in a polymeric layer. Accordingly, in certain embodiments the sensing element is redox active component that includes (1) Osmium-based mediator molecules attached by stable (bidente) ligands anchored to a polymeric backbone, and (2) glucose oxidase enzyme molecules. These two constituents are crosslinked together. Such sensing layers are described in, for example, U.S. Pat. No. 5,262,035, which is incorporated herein by reference in its entirety for all purposes.

Mass Transport Limiting Layer

The sensor may include a mass transport limiting layer (not shown), e.g., an analyte flux modulating layer, to act as a diffusion-limiting barrier to reduce the rate of mass transport of the analyte, for example, glucose or lactate, into the region around the working electrode. The mass transport limiting layers are useful in limiting the flux of an analyte to a working electrode in an electrochemical sensor so that the sensor is linearly responsive over a large range of analyte concentrations and is easily calibrated. Mass transport limiting layers may include polymers and may be biocompatible. A mass transport limiting layer may serve many functions, e.g., functionalities of a biocompatible layer and/or interferent-eliminating layer may be provided by the mass transport limiting layer.

In certain embodiments, a mass transport limiting layer is a membrane composed of crosslinked polymers containing heterocyclic nitrogen groups, such as polymers of polyvinylpyridine and polyvinylimidazole. Embodiments also include membranes that are made of a polyurethane, or polyether urethane, or chemically related material, or membranes that are made of silicone, silicone elastomer, and the like.

According to certain embodiments, a membrane is formed by crosslinking in situ a polymer, modified with a zwitterionic moiety, a non-pyridine copolymer component, and optionally another moiety that is either hydrophilic or hydrophobic, and/or has other desirable properties, in an alcohol-buffer solution. The modified polymer may be made from a precursor polymer containing heterocyclic nitrogen groups. For example, a precursor polymer may be polyvinylpyridine or polyvinylimidazole. Optionally, hydrophilic or hydrophobic modifiers may be used to "fine-tune" the permeability of the resulting membrane to an analyte of interest. Optional hydrophilic modifiers, such as poly(ethylene glycol), hydroxyl or polyhydroxyl modifiers, may be used to enhance the biocompatibility of the polymer or the resulting membrane. Mass transport limiting layers that may be adapted for use with present disclosure are described, e.g., in U.S. Pat. No. 6,932,894, the disclosure of which is incorporated herein by reference in its entirety for all purposes.

Accuracy

According to certain embodiments, analyte concentrations as determined by the signals detected from a dermal analyte sensor according to the present disclosure are within 80% of a reference value, such as within 85% of the reference value, including within 90% of the reference value, or within 95% of the reference value, or within 97% of the reference value, or within 98% of the reference value, or within 99% of the reference value. For example, for a given sensor, at least 80% of analyte signal from the sensor collected over a 14 day wear period are within 80% of a reference value as determined by a standard reference such as an in vitro test strip or YSI for glucose.

A high number of analyte concentrations as determined by the signals detected from a dermal analyte sensor are within Zone A of the Clarke Error Grid Analysis. For example, analyte concentrations as determined by the signals detected from a dermal analyte sensor are within Zone A of the Clarke Error Grid Analysis for 75% or more of the analyte sensors, such as 80% or more, or 90% or more, including 95% or more, or 97% or more, or 99% or more of the analyte sensors. In certain instances, concentrations as determined by the signals detected from the dermal analyte sensor that are within Zone A or Zone B of the Clarke Error Grid Analysis. For example, dermal analyte concentrations as determined by the signals detected from the analyte sensor that are within Zone A or Zone B of the Clarke Error Grid Analysis for 75% or more of the analyte sensors, such as 80% or more, or 90% or more, including 95% or more, or 97% or more, or 99% or more of the analyte sensors.

Calibration

Due at least in part to the stability and accuracy of the dermal sensing, the sensors may require no calibration or no user calibration after being positioned in the dermal layer, or no more than one calibration after positioned in the dermal layer. For example, a sensor may be factory calibrated and need not require further calibrating once dermally positioned. In certain embodiments, calibration may be required, but may be done without user intervention, i.e., may be automatic. In those embodiments in which calibration by the user is required, the calibration may be according to a predetermined schedule or may be dynamic, i.e., the time for which may be determined by the system on a real-time basis according to various factors, such as but not limited to glucose concentration and/or temperature and/or rate of change of glucose, etc.

Methods of Manufacturing Sensor Applicator Sets and Dermal Analyte Sensors

Embodiments of the present disclosure relate to methods of manufacturing dermal analyte sensors, devices containing these sensors, and dermal sensor applicator sets. The methods include disposing an insertion needle configured for dermal sensor insertion at an angle relative to a dermal sensor that includes a working electrode such that, during operation of the applicator set, the insertion needle creates an insertion path for the sensor as the sensor is being inserted into a subject.

In certain aspects, the dermal sensor is injection-molded from a plastic (e.g., a conductive plastic). A mold for the sensor may be designed to produce a sensor having any of the sensor dimensions described. The mold may further be designed to include shapes extending into or away from an internal cavity of the mold that, upon completion of the molding process, will result in the sensor having one or more structural features including, but not limited to, a groove having a shape and/or angle complementary to the insertion needle, a recess in which sensing reagent may be disposed, or any other structural feature that may improve the performance of (or provide additional functionalities to) an analyte sensor employing the sensor. Once the mold is designed and produced, the injection-molded sensor may be manufactured by heating a thermoplastic, thermosetting plastic, and/or any other material suitable for injection molding, injecting the heated material into the mold, and allowing the material to cool and harden to the configuration of the cavity. The molded sensor may then be retrieved from the mold, e.g., by disassembling the mold into two or more component parts.

According to certain embodiments, a dermal analyte sensor is an extruded sensor. That is, the sensor may be formed by coextruding a first conductive material, a second conductive material, and a dielectric material such that an extruded sensor having the first conductive material and the second conductive material electrically isolated by the dielectric material is formed. Extruded sensors and methods of manufacturing that may be adapted for use with the present disclosure are described in U.S. Publication No. 2010/0326842, the disclosure of which is incorporated herein by reference in its entirety for all purposes.

In other aspects, provided by the present disclosure are methods of manufacturing a dermal sensor that includes a working electrode. The methods include forming a dermal sensor having a dermal insertion length (the length of the dermal sensor that resides in the dermal space when the sensor is operatively positioned) of from 0.5 mm to 3 mm (e.g., from 1 mm to 2 mm), and disposing at least a first conducting material on all or a portion of the sensor, but at least at the dermal insertion length portion of a dermal sensor. In certain aspects, the methods further include disposing a second conducting material on all or a portion of the first conducting material. The first material (and when present, the second or more conductive materials) of conducting material may independently include a material selected from gold, carbon, platinum, ruthenium, palladium, silver, silver chloride, silver bromide, and combinations thereof.

Dermal sensors can be processed by punching a film of two or more electrically isolated conducting materials to form a sensor. According to this embodiment, a film that is an electrically isolated bi-layer (or tri layer, quad layer, etc.) may be formed where there is a layer of carbon-doped polymer followed by a layer of dielectric polymer and then a layer of carbon-doped polymer that is further doped with platinum or other suitable conducting material). This film can then be punched in the desired sensor shape and, optionally, laser machined to reveal one or more inner layers similar to a printed circuit board. In certain embodiments, a suitable polymer is doped with sensing reagents to obviate the need to dispense sensing reagents on the sensor/electrodes in an additional manufacturing step.

EXPERIMENTAL

Dermal Glucose Measurements Using Microprojection Dermal Electrodes

All three electrodes of a dermal glucose sensor were positioned in the dermal layer and no further. Another sensor was also used in which just a working electrode of a dermal sensor was positioned in the dermal layer and no further, and the reference and counter electrodes of this sensor were positioned in the subcutaneous space. The working electrodes of each sensor were fabricated as shown and described in FIG. 2. The reference electrodes and the counter electrodes were fabricated by coating Au-coated substrates with either Ag/AgCl to form a reference electrode, or carbon to form a counter electrode.

Wires attached to a potentiostat were attached to the base of the working electrode-bearing dermally implanted structure, as well as subcutaneously positioned counter and reference electrodes. A very small hole was made in the skin of the arm using a lancet. The dermal working electrode structure was carefully inserted into the hole just to the dermal layer and no farther, and adhered to the skin with adhesive. The corresponding reference and counter electrodes were inserted into the subcutaneous fat, to a depth of about 5 mm. As a control, a conventional three electrode subcutaneously positioned, transcutaneous in vivo glucose sensor was implanted in the arm adjacent to the dermal sensor, but all electrodes were in the subcutaneous layer.

Data was obtained simultaneously over a period of three days from both the dermal and subcutaneous sensors.

Figure 7:
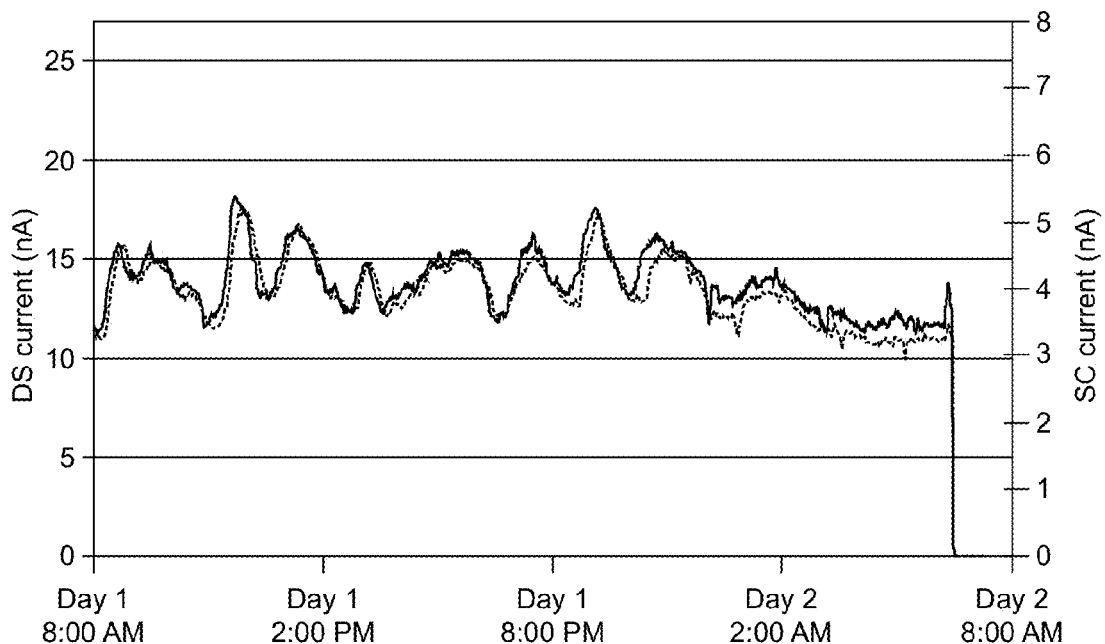
FIG. 7 provides, in Panels A-B, glucose concentration data obtained using a dermal glucose sensor according to one embodiment of the present disclosure, compared to data obtained using a subcutaneous glucose sensor. Measured current from the dermal sensor (DS) shown on the left axis of the graphs and the measured current from the subcutaneous sensor (SC) on the right axis of the graphs.
Figure 7:
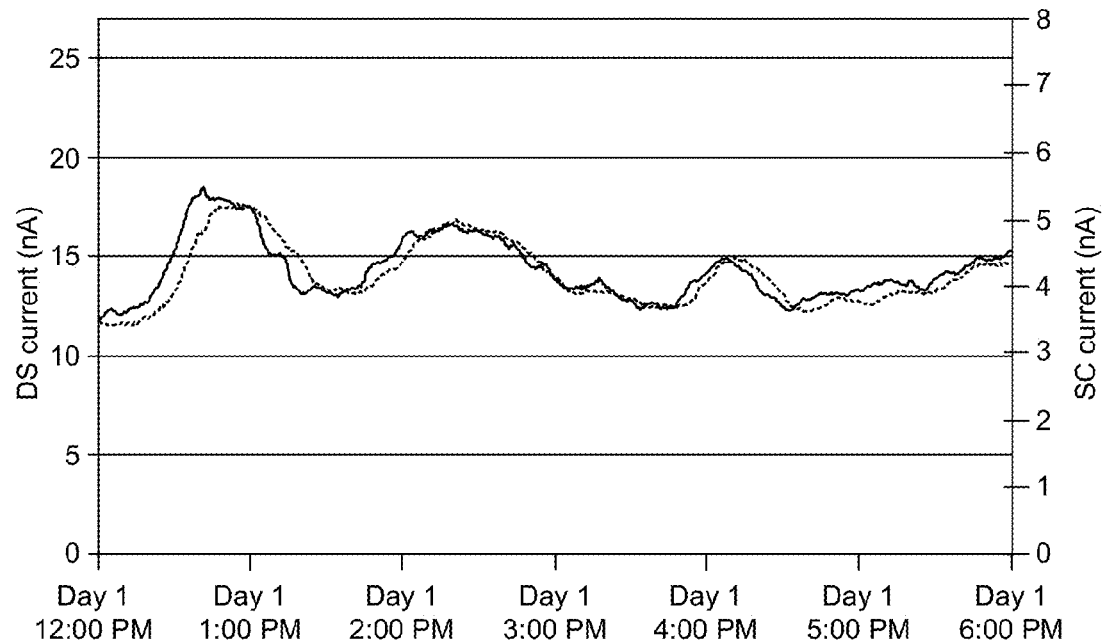

Results are shown in FIG. 7, Panel A. The results shown are those obtained from the dermal sensor in which the working electrode was positioned in the dermal space and the reference and counter electrodes were positioned in the subcutaneous space. Results obtained from the sensor in which three electrodes were positioned in the dermal space were similar. The graph of FIG. 7 shows results of day three of a three day simultaneous dermal/subcutaneous sensor experiment, with the measured current from the dermal sensor (DS) shown on the left axis and the measured current from the subcutaneous sensor (SC) on the right axis. The dermal sensor (solid line) leads the subcutaneous sensor (dashed line) by 5-8 minutes, depending on the peak. This is seen more clearly when expanding the data, as shown in FIG. 7, Panel B. For the peak on the left, at about 12:30 pm, the dermal sensor at 1 mm depth leads the subcutaneous sensor at 5 mm depth by about 7 minutes. Subsequent laboratory tests confirmed that the two sensors had approximately equal response times in-vitro, so the difference reflects the inherent differences between dermal sensors/sensing and subcutaneous sensors/sensing.

Although the foregoing subject matter has been described in some detail by way of illustration and example for purposes of clarity of understanding, it is readily apparent to those of ordinary skill in the art in light of the present teachings that certain changes and modifications may be made thereto without departing from the spirit or scope of the appended claims.

Accordingly, the preceding merely illustrates the principles of the devices and methods described herein. It will be appreciated that those skilled in the art will be able to devise various arrangements which, although not explicitly described or shown herein, embody the principles of the present subject matter and are included within its spirit and scope. Furthermore, all examples and conditional language recited herein are principally intended to aid the reader in understanding these principles and the concepts contributed by the inventors to furthering the art, and are to be construed as being without limitation to such specifically recited examples and conditions. Moreover, all statements herein reciting principles, aspects, and embodiments of the present subject matter as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present subject matter, therefore, is not intended to be limited to the exemplary embodiments shown and described herein, but rather by the claims submitted herewith and in the future.

What is claimed is:

1. A method of using an applicator set to sense an analyte level of a subject, the applicator set comprising a base, an insertion needle, and a dermal sensor, the method comprising:

inserting a tip portion of an insertion needle and a tip portion of a dermal sensor, together, into a dermal layer of a skin site of a subject such that the dermal sensor is inserted into but not through the dermal layer, wherein a longitudinal central axis along the tip portion of the insertion needle is angled relative to a longitudinal central axis along the tip portion of the dermal sensor and the tip portion of the insertion needle creates an insertion path for the dermal sensor as the insertion needle is inserted into the skin site; and sensing an analyte level in the dermal layer of the skin site with the dermal sensor.

2. The method of claim 1, further comprising removing the insertion needle after inserting the dermal sensor into the dermal layer of the subject.

3. The method of claim 1, wherein the longitudinal central axis along the tip portion of the insertion needle is disposed at an angle of 7° to 15° relative to the longitudinal central axis along the tip portion of the dermal sensor.

4. The method of claim 1, wherein the longitudinal central axis along the tip portion of the insertion needle is disposed at an angle of 9° to 13° relative to the longitudinal central axis along the tip portion of the dermal sensor.

5. The method of claim 1, wherein the longitudinal central axis along the tip portion of the insertion needle is disposed at an angle of 5° to 20° relative to the longitudinal central axis along the tip portion of the dermal sensor.

6. The method of claim 1, wherein a distal portion of the dermal sensor comprises a groove having a shape complementary to the insertion needle.

7. The method of claim 1, wherein inserting the dermal sensor comprises inserting a sensing region of a working electrode of the dermal sensor to a depth of 0.5 mm to 3 mm relative to an external skin surface of the subject.

8. The method of claim 1, wherein inserting the dermal sensor comprises inserting a sensing region of a working electrode of the dermal sensor to a depth of 1 mm to 2 mm relative to an external skin surface of the subject.

9. The method of claim 1, wherein the tip portion of the insertion needle is non-bladed.

10. The method of claim 9, wherein the tip portion of the insertion needle has a pointed termination on the longitudinal central axis of the insertion needle.

11. The method of claim 10, wherein the tip portion of the insertion needle does not have an internal space.

12. The method of claim 11, wherein the tip portion of the insertion needle is not covered.

13. The method of claim 1, wherein the insertion needle has a diameter between 0.1 mm and 0.5 mm.

14. The method of claim 1, wherein the insertion needle has a length of between 1.5 mm and 25 mm.

15. The method of claim 1, wherein an inserted portion of the sensor has a length of between 0.5 mm and 3 mm.

16. The method of claim 1, wherein an inserted portion of the sensor has a length of between 1 mm and 2 mm.

17. The method of claim 1, wherein a distal end of the sensor comprises a molded recess to accept analyte-sensing reagents.

18. The method of claim 1, wherein the insertion needle is adjacent to the dermal sensor in a side-by-side arrangement.

19. The method of claim 1, wherein the tip portion of the insertion needle and a distal end of the dermal sensor are co-localized.

20. The method of claim 1, further comprising inserting the insertion needle and the dermal sensor at a non-normal angle to the skin site.

21. The method of claim 1, wherein the sensing of the analyte level is performed by a user, and the user uses the dermal sensor to sense analyte levels with no calibration being performed after inserting the insertion needle and the dermal sensor.

22. A method of using an applicator set to sense an analyte level of a subject, the applicator set comprising a base, an insertion needle, and a dermal sensor, the method comprising:

inserting a tip portion of an insertion needle and a tip portion of a dermal sensor, together, into a dermal layer of a skin site of a subject such that the dermal sensor is inserted into but not through the dermal layer, wherein the dermal sensor is adjacent to the insertion needle but not positioned within the insertion needle, and wherein a longitudinal central axis along the tip portion of the insertion needle is angled relative to a longitudinal central axis along the tip portion of the dermal sensor; and sensing an analyte level in the dermal layer of the skin site with the dermal sensor.

23. The method of claim 22, further comprising removing the insertion needle after inserting the dermal sensor into the dermal layer of the subject.

24. The method of claim 22, wherein the longitudinal central axis along the tip portion of the insertion needle is disposed at an angle of 5° to 20° relative to the longitudinal central axis along the tip portion of the dermal sensor.

25. The method of claim 22, wherein a distal portion of the dermal sensor comprises a groove having a shape complementary to the insertion needle.

26. The method of claim 22, wherein inserting the dermal sensor comprises inserting a sensing region of a working electrode of the dermal sensor to a depth of 0.5 mm to 3 mm relative to an external skin surface of the subject.

27. The method of claim 1, wherein the insertion needle and the dermal sensor are inserted into the dermal layer without being in a male-female relationship.

28. The method of claim 22, wherein the insertion needle and the dermal sensor are inserted into the dermal layer without being in a male-female relationship.

29. The method of claim 1, wherein the longitudinal central axis along the tip portion of the insertion needle is at a non-normal angle to a surface of the skin and the longitudinal central axis along the tip portion of the dermal sensor is at a normal angle to the surface of the skin.

* * * * *